(12) United States Patent
Snow et al.

(10) Patent No.: US 6,482,639 B2
(45) Date of Patent: Nov. 19, 2002

(54) MICROELECTRONIC DEVICE AND METHOD FOR LABEL-FREE DETECTION AND QUANTIFICATION OF BIOLOGICAL AND CHEMICAL MOLECULES

(75) Inventors: Eric S. Snow, Springfield, VA (US); Martin Peckerar, Silver Spring, MD (US); Leonard M. Tender, Bethesda, MD (US); Stephanie J. Fertig, Springfield, VA (US); Frank K. Perkins, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/886,051

(22) Filed: Jun. 22, 2001

(65) Prior Publication Data

US 2002/0012937 A1 Jan. 31, 2002

Related U.S. Application Data

(60) Provisional application No. 60/213,471, filed on Jun. 23, 2000.

(51) Int. Cl.[7] .............................. C12M 1/34; C12Q 1/68; C12P 19/34; C07H 21/02; H01L 23/58
(52) U.S. Cl. ..................... 435/287.2; 435/6; 435/7.1; 435/91.1; 435/91.2; 536/22.1; 536/23.1; 536/24.3; 536/24.31; 536/24.32; 438/49
(58) Field of Search ............................. 435/6, 7.1, 91.1, 435/91.2, 287.2; 536/22.1, 23.1, 24.3–24.33; 438/49

(56) References Cited

U.S. PATENT DOCUMENTS

| 4,020,830 | A |   | 5/1977  | Johnson et al. |
| 4,198,851 | A |   | 4/1980  | Janata |
| 4,931,851 | A |   | 6/1990  | Sibbald et al. |
| 5,035,791 | A |   | 7/1991  | Battilotti et al. |
| 5,116,481 | A |   | 5/1992  | Ozawa et al. |
| 5,466,348 | A |   | 11/1995 | Holm-Kennedy |
| 5,543,024 | A |   | 8/1996  | Hanazato et al. |
| 6,413,792 | B1 | * | 7/2002  | Sauerr et al. ................. 438/49 |

OTHER PUBLICATIONS

IEDM Technical "An Active Microelectronic Transducer for enabling Label–Free Miniaturized Chemical Sensors" p. 407–410 Dec. 10, 2000.
Provisional Application–60/213,471"Capacitance Coupled Field Effect Transistor" Filed Jun. 23, 2000.

* cited by examiner

Primary Examiner—Jeffrey Siew
(74) Attorney, Agent, or Firm—John J. Karasek; Joseph T. Grunkemeyer

(57) ABSTRACT

Molecular recognition-based electronic sensor, which is gateless, depletion mode field effect transistor consisting of source and drain diffusions, a depletion-mode implant, and insulating layer chemically modified by immobilized molecular receptors that enables miniaturized label-free molecular detection amenable to high-density array formats. The conductivity of the active channel modulates current flow through the active channel when a voltage is applied between the source and drain diffusions. The conductivity of the active channel is determined by the potential of the sample solution in which the device is immersed and the device-solution interfacial capacitance. The conductivity of the active channel modulates current flow through the active channel when a voltage is applied between the source and drain diffusions. The interfacial capacitance is determined by the extent of occupancy of the immobilized receptor molecules by target molecules. Target molecules can be either charged or uncharged. Change in interfacial capacitance upon target molecule binding results in modulation of an externally supplied current through the channel.

14 Claims, 2 Drawing Sheets

MICROELECTRONIC DEVICE AND METHOD FOR LABEL-FREE DETECTION AND QUANTIFICATION OF BIOLOGICAL AND CHEMICAL MOLECULES

This application claims the benefit of provisional application U.S. Ser. No. 60/213,471, filed Jun. 23, 2000, the disclosure of which is incorporated herein by reference.

BACKGROUND OF THE INVENTION

1. Field of the Invention

The present invention is a microelectronics-based sensor, specifically, a microelectronics-based transducer for molecular recognition-based sensors for detection or quantification of charged and uncharged target molecules.

2. Description of the Background Art

Molecular recognition-based sensors are important research tools because of the wide range of target molecules for which receptors can be harvested or synthesized. They have proven indispensable in genomic and pharmaceutical research and development configured in high-density arrays of thousands of individual sensor elements, each element being responsive to a specific target molecule by immobilization of a corresponding molecular receptor. Such arrays enable simultaneous detection of thousands of target molecules from mixtures. Currently, the detection of chemical and biochemical species utilizing molecular recognition elements is dependent upon the use of labels or reagents including, but not limited to, fluorophores, radioisotopes, and enzymes that generate a measurable signal to report binding of target molecule by the receptor molecule. The use of such labeling reagents is labor intensive, equipment intensive and is prone to human and equipment error. Further, the difficulty in the use of labeling reagents has prohibited widespread application of molecular receptor recognition-based sensing outside research and development environments. Further, the use of labeling reagents precludes real time diagnostics in the field.

Further, the current methods for the detection of chemical and biochemical species utilizing microelectronics-based transducers (i.e., field effect transistors (FETs)) depend upon a change in FET gate charge as the sensing approach. Many target molecules of interest are uncharged, therefore they are not detectable using the current microelectronics-based transducers.

Therefore, there is a strong need in the field to provide devices and methods capable of sensitive and accurate detection of target molecules without the use of labeling reagents. Further there is a strong need for devices and methods for label-free assays capable of real-time analysis in vitro and in vivo. Further, there is a strong need for arrays for simultaneous detection of multiple target molecules without the use of labeling reagents.

Further, there is a strong need in the art for devices and methods to detect both charged and uncharged target molecules.

OBJECTS OF THE INVENTION

Accordingly, it is an object of the present invention to provide molecular recognition-based electronic devices and methods capable of sensitive and accurate detection of target molecules without the use of labeling reagents.

It is another object of the present invention to provide molecular recognition-based electronic devices and methods of label-free assays capable of real-time analysis in vitro and in vivo.

It is another object of the present invention to provide for arrays for simultaneous detection of multiple target molecules without the use of labeling reagents.

It is another object of the present invention to provide devices and methods to detect both charged and uncharged target molecules.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

According to the present application, the foregoing and other objects and advantages are attained by providing a sensor comprising a gateless, depletion-mode, field effect transistor (FET) having a source implant and a drain implant that are spatially arranged within a semiconductor structure and separated by an active channel. A dielectric layer covers the active channel between the source and drain, and the dielectric layer surface is modified with immobilized molecular receptors. The receptor-modified dielectric layer surface contacts a sample solution. The immobilized molecular receptors are available to bind target molecules present in the sample solution. The FET-based sensor is imbedded in a substrate with its receptor-modified dielectric layer exposed, and electrical connections are available for applying bias between the source and drain and between a reference electrode in the sample solution and the FET semiconductor substrate. The sensor detects the presence of target molecules in the sample solution by measuring the change in current between the source and drain that occurs due to either the change in capacitance of the receptor-modified dielectric film/sample solution interface when target molecules bind to the molecular receptors, or when charged molecules bind to the receptor-modified dielectric film/sample solution interface.

Another aspect of the invention provides for a sensor array, with at least two sensors as described above. Each sensor is fabricated into a common substrate with each individual sensor's respective receptor-modified dielectric layer exposed. Each sensor is individually modified with molecular receptors. The sensors operate in parallel and are individually electrically addressable.

Another aspect of the invention provides for a method for detecting a target molecule species by contacting the sensor of the present application with a sample solution, which creates an interface between the sample solution and the receptor-modified dielectric layer. The binding of target molecules to the receptor molecules immobilized on the dielectric layer changes the interfacial capacitance that exists between the sample solution and the receptor modified dielectric layer. This change of interfacial capacitance changes the conductivity of the active channel. The conductivity of the active channel modulates an externally supplied current flowing through the active channel when a terminal bias is applied between the source and the drain. The modulation of the externally supplied current flowing through the active channel can be measured to detect binding of the target molecules to the molecular receptors. The methods and devices of the invention remove the dependency of molecular-recognition-based sensors on labeling reagents, which enables a wider scope of practical and worthwhile utilization of recognition-based sensors. The removal of dependency of molecular recognition-based sensors on labeling reagents also makes possible in vivo application of miniaturized sensor arrays for medical research and real time treatment assessment.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

The device of the present application is a depletion mode field effect transistor consisting of source and drain n+ implants, an n− depletion-mode channel implant, and an oxide/nitride insulating bilayer. In conventional embodiments of FET technology, a conductive layer, i.e. a gate, is installed above the active channel. No such gate is present in the present invention, therefore, this device is referred to as a "gateless" FET. This oxide/nitride layer can be modified with immobilized molecular receptors including, but not limited to, proteins, antibodies, antigens, peptides or oligonucleotides. The molecular receptors can be immobilized on the dielectric layer by any of several processes, including, but not limited to, providing a thiol reactive layer by either AuPd plasma sputter co-deposition or Cr/Au evaporation.

The observed channel conductivity responds to changes in gate-channel capacitance as well as solution potential, and such response is immediate and substantial. In practice, a sample solution containing no, one, or more target molecule species is allowed to contact the gate region. A reference electrode is inserted in the solution. The consequent solution potential (with respect to the substrate) represents a gate bias that couples capacitively to the active channel, itself biased by the source and drain applied potentials. Binding of target molecules (if present) by the immobilized receptor molecules reduces the capacitive coupling between the channel and the solution, and thus channel conductivity. A device such as this can be miniaturized and fabricated by standard microelectronic techniques in high-density arrays for simultaneous detection of multiple target molecules, with sensitivity increasing with miniaturization. Examples of potential uses include, but are not limited to, a genetic assay based in a point of care environment requiring limited instrumentation and performed by non-technically trained personnel to provide important genetic information rapidly and cost-effectively.

Figure 1:
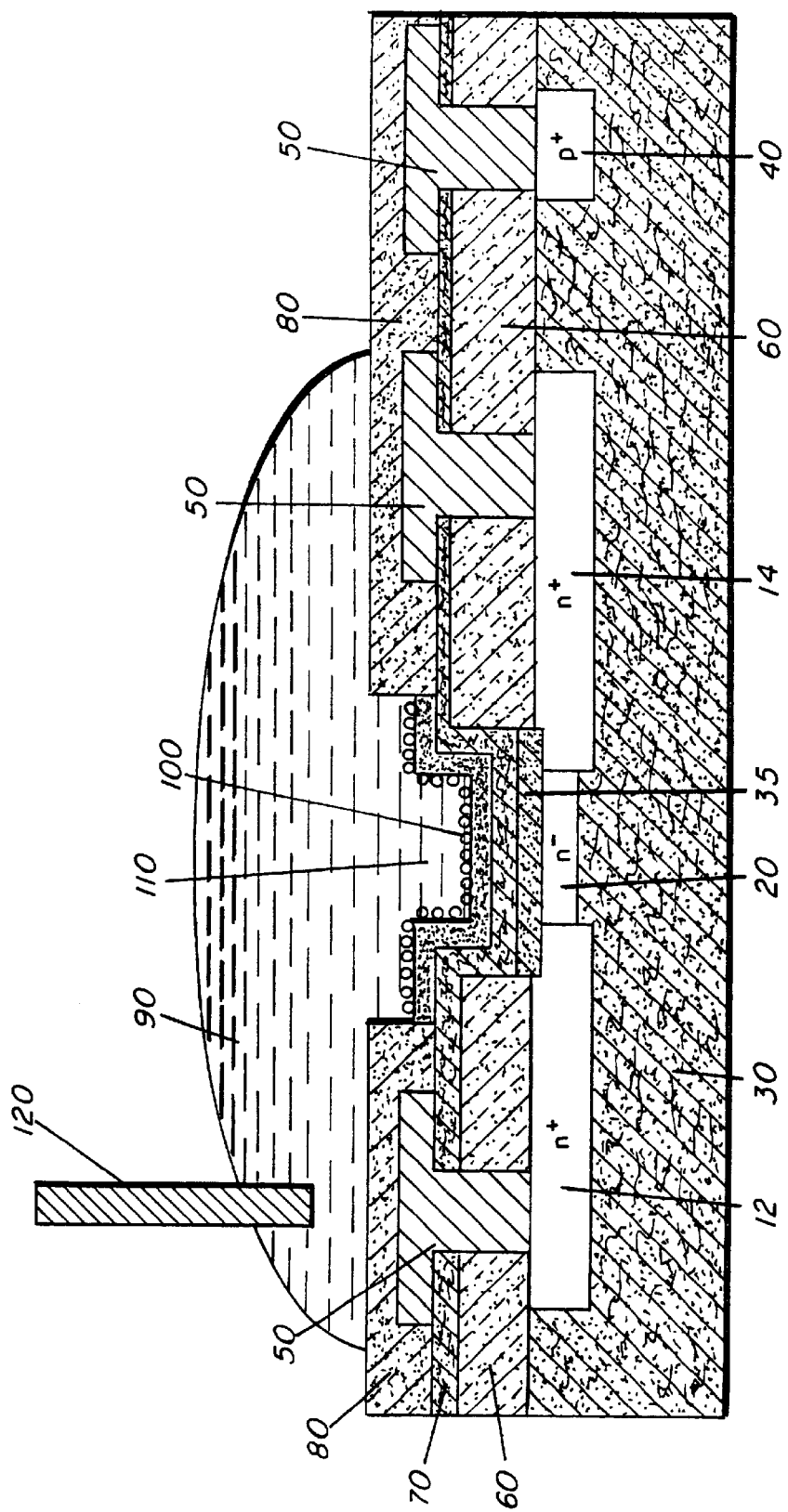
FIG. 1. is a schematic, not to scale, cross sectional representation of a single sensor.

A schematic, not to scale, cross-section of the device is shown in FIG. 1. Semiconducting regions of n+ carrier type, including, interchangeably, a source 12 and a drain 14, are fabricated into a semiconducting substrate material 30. An active semiconducting channel 20 is between the source 12 and drain 14. A SiO$_2$ "gate oxide" layer 35 covers and is in contact with the active channel 20. A body contact 40 is also fabricated into the substrate 30. Electrodes 50 connect to the source 12, drain 14, and body contact 40. A second SiO$_2$ layer 60 isolates the electrodes 50 from the substrate 30. A Si$_3$N$_4$ layer 70 covers the first SiO$_2$ layer 35 and the second SiO$_2$ layer 60. A third SiO$_2$ layer 80 isolates the electrodes 50 from the test solution 90. Molecular receptors 100 cover the active sensing region 110. A reference electrode 120 is used to bias test solution 90.

The sensor described here is based upon a depletion-mode (normally on) field-effect transistor. The use of this type of FET is important in that the base-line bias over the active channel of the FET is supplied by the sample solution. The sample solution itself effectively provides the gate bias, and it is not required that a threshold voltage be overcome in order to supply source-to-drain current. The target molecule may be therefore be either charged or uncharged.

In a conventional n-channel depletion mode MOSFET in the ohmic state, the source-drain current $i_{SD}$ is given by $$i_{SD} = \frac{k}{2}[2(v_{GS} - V_{th})v_{SD} - v_{SD}^2],$$

where the transconductance parameter k is given by $$k = \frac{W}{L}\mu_n C_{ox},$$

$\mu_n$ is the electron mobility (1900 cm$^2$V$^{-1}$ s$^{-1}$ in Si), $C_{ox}$ is the gate oxide capacitance per unit area, $v_{GS}$ and $v_{SD}$ are the gate-source and drain-source biases, respectively, and $V_{th}$ is the threshold bias of the device. Here, where the gate "oxide" is ultimately a bilayer, the net capacitance is given as a series capacitor network by $$C = \left[\sum_{i=1}^{n} \frac{d_i}{\varepsilon_0 \varepsilon_i}\right]^{-1}$$

Substituting values for layer thickness given above, using values for the dielectric constant $\epsilon_i$ of 3.0 and 12.7 for SiO$_2$ and Si$_3$N$_4$, respectively, and for $\epsilon_0$ the value 8.85×10$^{-15}$ F cm$^{-2}$, the layer capacitance is 4.8 nF cm$^{-2}$. Thus we find an expected intrinsic (untreated, dry) value for k in our devices of 39 µA V$^{-1}$. Collecting terms, we find that $$i_{SD} = C_{ox}\frac{W}{L}\frac{\mu_n}{2}[2(v_{GS} - V_{th}) - v_{SD}]v_{SD}.$$

This indicates several features of the utility of a depletion mode FET as the basis for this device, essentially functioning as a first stage signal transducer. An accumulation of even low levels of charge on the gate affects the current equivalent to a change in gate bias. A change in capacitance due to an accumulation of molecular species equivalent to a change in gate oxide thickness has a linear effect on current. In comparison to an enhancement mode FET, a substantial current flows even a zero gate bias, decreasing the requisite power requirements and increasing the operational flexibility.

In the configuration in which these devices are used, the channel may be thought of as one electrode in an electrochemical cell. As such, the gate capacitance is a combination of the gate oxide, any molecular layer on the surface, and the double layer capacitance of the solution used during testing at both the device surface as well as the reference electrode. Effects, including, but not limited to, changes in temperature, ionic strength, and pH, attributable solely to changes in the test solution (or equivalently at the reference electrode-solution interface) are observable dynamically in many ways including, but not limited to, the use of control devices modified with receptors whose targets are not present in solution.

The immobilized biological and chemical molecular receptors of the FET include, but are not limited to, single strand DNA, single strand PNA, binding proteins, antibodies, DNA aptamers, PNA aptamers, RNA aptamers, antigens, enzymes, peptides, chelating molecules, molecular assemblies with chelating functional groups, and reagents for covalent attachment of target molecules.

The charged or uncharged biological and chemical target molecules of the FET include, but are not limited to, single strand DNA, proteins, antigens, bacteria, viruses, biological molecules with functional groups that are covalently bound to receive species, chemical species for which biological receptors exist, chemical species for which PNA receptors exist, chemical species for which RNA receptors exist, chemical species for which DNA receptors exist, chemical species which are bound by chemical chelators, and metal ions.

The advantages of the invention include, but are not limited to, the ability to integrate the sensor with a preamplifier, to make a sensor as small as 2 $\mu$m by 2 $\mu$m ($10^{-8}$ $cm^2$) which is capable of detecting one or more target molecules, to configure arrays of sensors containing thousands of individually addressable and discrete sensor elements occupying a total active area as small as 1 $cm^2$, and to provide for label-free continuous multi-analyte detection of charged and uncharged target molecules that has high sensitivity, high resolution, and is cost-effective. The FET-based sensor of the present application provides electrical gain. Therefore, a small change in the extent of occupancy of the immobilized receptors by target molecules modulates a large (microamp to milliamp) externally supplied current. The FET-based sensor integrates the pre-amplifier with the sensor element therefore significantly reducing electrical noise. Multiple sensing elements allow for signal averaging and utilization of cross-reactive responses.

EXAMPLES

The following examples illustrate certain embodiments of the present invention. However, they are not to be construed to limit the scope of the present invention in any way.

Example 1

A source and drain were formed by a P implant in a semiconductor structure at 80 keV to an areal density of $1 \times 10^{15}$ $cm^{-2}$. The channel region is 32 $\mu$m×140 $\mu$m and P implanted at 60 keV to an areal density of $6 \times 10^{11}$ $cm^{-2}$. Body contacts were formed by B implantation at 80 keV to $1 \times 10^{15}$ $cm^{-2}$. A 63 nm thermal oxide layer was followed by a 30 nm LPCVD $Si_3N_4$ layer. Following a Cr/Au contact metallization, a 600 nm APCVD oxide layer was formed over all. The present example used 36 devices per wafer arranged in 9 groups of 4 on a 6.5 mm pitch. Each device had a separate and independent source and drain contact. Additionally, 14 gated and ungated test structures were included on the wafer for use as reference standards and process and instrumentation diagnostic tools.

Immobilization procedures have relied on the facile attachment of thiol (—S) ligands to Au evaporated onto the dielectric layer by means of molecular self-assembly. To accomplish this, a patterned photoresist layer defined the gate region for a thin (<10 nm) PdAu layer sputter deposited on the wafer and subsequently lifted off in acetone. In one example, a dodecane thiol layer was formed by immersion into a dilute solution of the precursor in ethanol. In another example, a 15-mer sequence of a DNA single strand, modified with a thiol ligand, was self-assembled from a binding buffer solution onto the gate area.

Before use, a Plexiglas fluid cell was fastened to the wafer to confine a phosphate buffer solution (PBS) to each cell, allowing independent testing and dosing. An Ag reference electrode was used to establish the solution potential. Testing used a Keithley 617 electrometer to establish the source drain bias ($v_{SD}$) and measure the source drain current ($i_{SD}$), and a second Keithley 617 electrometer was used to establish the gate (reference electrode) bias ($v_{GS}$). The devices were simultaneously contacted by a custom epoxy ring probe card and demultiplexed into the electrometer in a Keithley 7002 matrix switcher and 7012 4×10 matrix cards.

Dodecane thiol ($C_{12}H_{25}HS$) creates an inert, non-reactive surface that can be used to observe non-specific adsorption of proteins. Here, streptavidin was used as the target molecule, dissolved at 1 $\mu$g/ml in PBS and allowed to absorb overnight from solution to the surface. Protein species will absorb to the alkane surface nonspecifically. The addition of streptavidin to the cell was observed to lower $i_{SD}$ by 35–45%. The absorption of protein to the dodecane surface displaces solution ionic charge from the surface, lowering the interfacial capacitance, and thus $i_{SD}$.

Example 2

Figure 2:
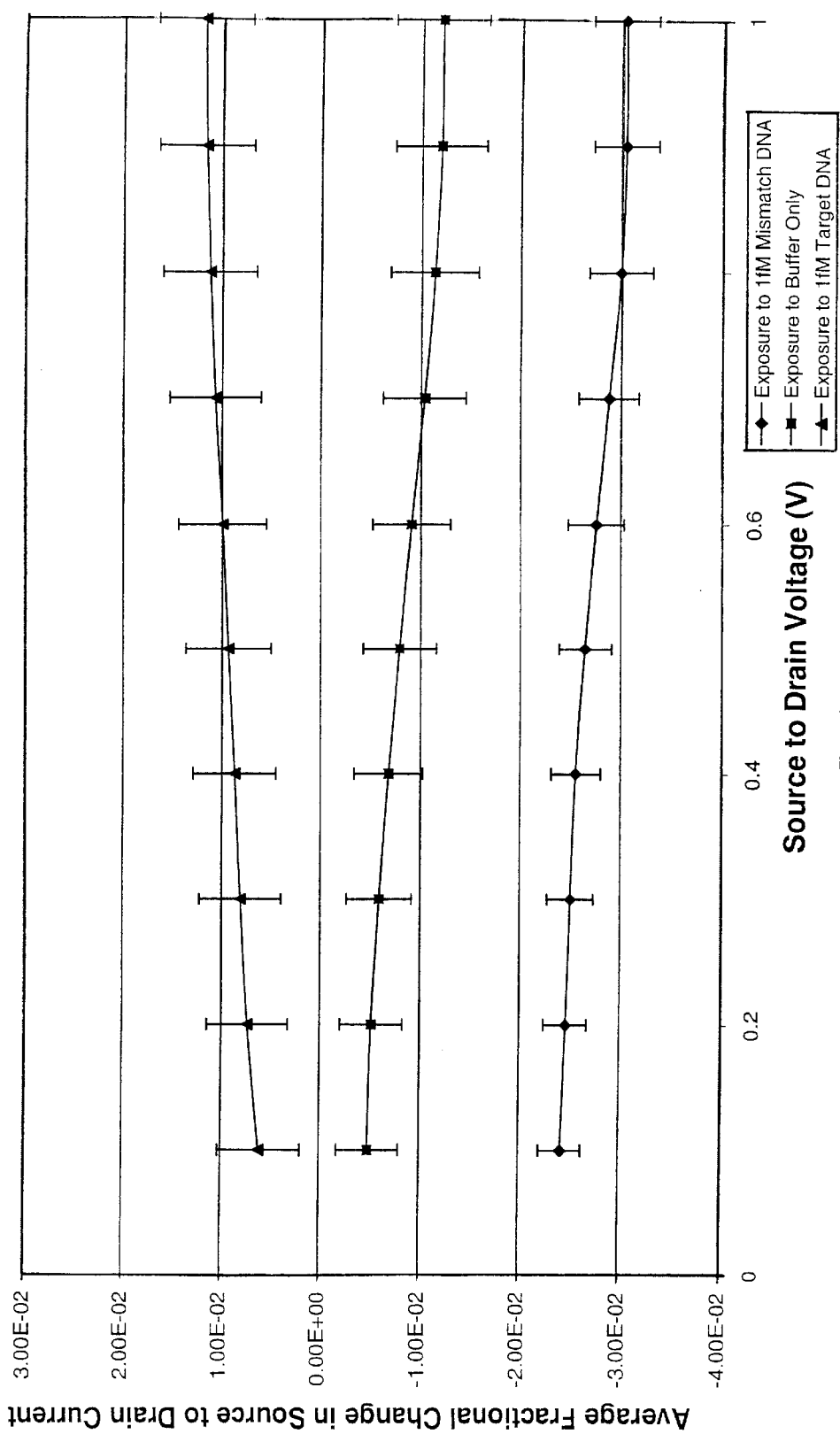
FIG. 2 shows the typical response of a 100 µm-dimensional electronic sensor in aqueous solutions.

In contrast to Example 1, the gold modified dielectric layer was in turn modified with thiol terminated single strand DNA. The sensors were exposed to either a solution with 1 fM of single stranded DNA that was complementary to the DNA on the surface, a solution with 1 fM of single stranded DNA that contained a one base pair mismatch to the DNA on the surface, or a blank buffer solution. At this concentration, response to the target DNA was a drop in current of 1.2+/−0.5%, while the current increased 1.2+/−0.5% for the devices exposed to the control buffer solution and 3.0+/−0.3% for those exposed to the mismatch DNA. FIG. 2 shows the typical response of the sensors to the three different solutions plotted as the fractional change in current. The fractional change in source to drain current is ($i_{SD}^{before} - i_{SD}^{after})/i_{SD}^{before}$.

It is understood that the foregoing detailed description is given merely by way of illustration and that many variations may be made therein without departing from the spirit of this invention.

What is claimed is:

1. A sensor for detecting target molecules comprising:
   a depletion-mode field effect transistor (FET) having a source implant and a drain implant that are spatially arranged within a semiconductor structure, said source and drain being separated by an active channel, said field effect transistor being gateless;
   a dielectric layer covering said active channel, said dielectric layer having a bottom surface in contact with the active channel and a top surface in contact with a sample solution, said top surface being surface modified with immobilized molecular receptors, said immobilized molecular receptors being available to bind target molecules present in the sample solution, wherein said FET is imbedded in a substrate with said receptor modified dielectric layer exposed; and
   a reference electrode in contact with said sample solution, wherein said substrate is biased with respect to said reference electrode.

2. A sensor as in claim 1 wherein said immobilized molecular receptors are biological receptors.

3. A sensor as in claim 2 wherein said immobilized molecular receptors are selected from the group consisting of single strand DNA, single strand PNA, binding proteins, antibodies, DNA aptamers, PNA aptamers, RNA aptamers, antigens, enzymes, and peptides.

4. A sensor as in claim 1 wherein said immobilized molecular receptors are non-biological receptors.

5. A sensor as in claim 4 wherein said immobilized molecular receptors are selected from the group consisting of chelating molecules, molecular assemblies with chelating functional groups, and reagents for covalent attachment of target molecules.

6. A sensor as in claim 1 wherein said target molecules are charged.

7. A sensor as in claim 1 wherein said target molecules are uncharged.

8. A sensor as in claim 1 wherein said target molecules are biological molecules.

9. A sensor as in claim 8 wherein said target molecules are selected from the group consisting of single strand DNA, proteins, antigens, bacteria, viruses, and biological molecules with functional groups that are covalently bound to reactive species.

10. A sensor as in claim 1 wherein said target molecules are non-biological molecules.

11. A sensor as in claim 10 wherein said target molecules are selected from the group consisting of chemical species for which biological receptors exist, chemical species for which PNA receptors exist, chemical species for which RNA receptors exist, chemical species for which DNA receptors exist, chemical species which are bound by chemical chelators, and metal ions.

12. A sensor array, comprising:
   at least two sensors as in claim 1, said sensors being fabricated onto a substrate with each individual said sensor's respective said receptor modified dielectric layer exposed to said sample solution, said each individual sensor being individually modified with a molecular receptor, said sensors operating in parallel, each sensor being individually electrically addressable.

13. A method for detecting a target molecule species comprising the steps of:
   contacting the sensor of claim 1 with a sample solution wherein an interface between said sample solution and said receptor modified dielectric layer of the sensor is created, wherein an interfacial capacitance exists at said interface between said sample solution and said receptor modified dielectric layer;
   placing said reference electrode in contact with said sample solution;
   applying a terminal bias between the reference electrode and the substrate;
   applying a terminal bias between said source and said drain, wherein said interfacial capacitance is changed by the binding of target molecules to said receptor molecules immobilized on said dielectric layer by displacement of a solution ionic charge, wherein said change of interfacial capacitance changes the conductivity of the active channel, wherein the conductivity of the active channel modulates the externally supplied current flowing through said active channel when said externally supplied current is caused by a terminal bias applied between said source and said drain; and
   measuring the change in current between the source and drain.

14. A method for detecting and quantifying at least two target molecule species comprising the steps of:
   contacting the sensor array of claim 12 in said sample solution, wherein an interface between said sample solution and each individual sensor's receptor-modified dielectric layer is created, wherein an interfacial capacitance exists at said interfaces between said sample solution and said each individual sensor's receptor-modified dielectric layer;
   placing the reference electrode in contact with said sample solution;
   applying a terminal bias between the reference electrode and the substrate;
   applying an terminal bias between each individual sensor's said source and said drain, wherein said interfacial capacitance is changed by the binding of target molecules to said receptor molecules immobilized on said dielectric layer by displacement of a solution ionic charge, wherein said change of interfacial capacitance changes the conductivity of the active channel, wherein the conductivity of the active channel modulates the externally supplied current flowing though said active channel when said terminal bias is applied between said source and said drain; and
   measuring the change in current between each individual sensor's source and drain.

* * * * *